US012622855B1

(12) United States Patent
Schwartz

(10) Patent No.: US 12,622,855 B1
(45) Date of Patent: May 12, 2026

(54) HYPERPIGMENTATION TREATMENT CREAM AND SERUM

(71) Applicant: Procell Therapies, LLC, Austin, TX (US)

(72) Inventor: Mitchell Schwartz, Clearwater Beach, FL (US)

(73) Assignee: Procell Therapies, LLC, Austin, TX (US)

( * ) Notice: Subject to any disclaimer, the term of this patent is extended or adjusted under 35 U.S.C. 154(b) by 0 days.

(21) Appl. No.: 19/003,482

(22) Filed: Dec. 27, 2024

Related U.S. Application Data

(60) Provisional application No. 63/615,034, filed on Dec. 27, 2023.

(51) Int. Cl.
| | |
|---|---|
| *A61K 8/44* | (2006.01) |
| *A61K 8/42* | (2006.01) |
| *A61K 8/46* | (2006.01) |
| *A61K 8/66* | (2006.01) |
| *A61Q 19/02* | (2006.01) |

(52) U.S. Cl.
CPC .................. *A61K 8/44* (2013.01); *A61K 8/42* (2013.01); *A61K 8/46* (2013.01); *A61K 8/66* (2013.01); *A61Q 19/02* (2013.01); *A61K 2800/48* (2013.01); *A61K 2800/51* (2013.01)

(58) Field of Classification Search
None
See application file for complete search history.

(56) References Cited

U.S. PATENT DOCUMENTS

| | | | | |
|---|---|---|---|---|
| 10,835,572 B2 * | 11/2020 | Haga | ......................... | A61K 8/44 |
| 2014/0017182 A1 * | 1/2014 | Trumbore | ................ | A61K 8/66 |
| | | | | 424/59 |
| 2014/0112877 A1 * | 4/2014 | Niki | ..................... | A61K 8/4946 |
| | | | | 424/62 |
| 2016/0296443 A1 * | 10/2016 | Nalabolu | ............. | A61K 8/9789 |

FOREIGN PATENT DOCUMENTS

| | | | | | |
|---|---|---|---|---|---|
| WO | WO-2021186243 A1 * | 9/2021 | ............... | A61K 8/64 |
| WO | WO-2024056568 A1 * | 3/2024 | ............. | A61Q 19/02 |

* cited by examiner

*Primary Examiner* — Nicole P Babson
*Assistant Examiner* — Lori K Mattison
(74) *Attorney, Agent, or Firm* — Downs Rachlin Martin PLLC

(57) ABSTRACT

Compositions for skin creams and serums are provided for treating skin hyperpigmentation, the compositions including cysteamine, tranexamic acid, niacinamide, tetrapeptide 30, DNA repair enzymes, and human growth factors. A formulation for the skin cream or serum includes 5% cysteamine by weight, 5% tranexamic acid by weight, 4% niacinamide by weight, 1% tetrapeptide 30 by weight, in which the tetrapeptide 30 includes the following four amino acids linked together: L-prolyl-L-lysyl-L-alpha-glutamyl-L-lysine. In addition, the cream or serum includes DNA repair enzymes, including 1% phytosomes, 0.3 to 1% roxisomes, and 1% ultrasomes. Further, the composition may include recombinant human growth factors.

2 Claims, No Drawings

HYPERPIGMENTATION TREATMENT CREAM AND SERUM

RELATED APPLICATION DATA

This application claims the benefit of priority of U.S. Provisional Patent Application Ser. No. 63/615,034, filed Dec. 27, 2023, and titled "Hyperpigmentation Cream and Serum," which is incorporated by reference herein in its entirety.

FIELD

The present disclosure relates to the field of skin care compositions, and more specifically to creams or serums for treating hyperpigmentation.

BACKGROUND

While the use of growth factors and other chemicals to treat aging skin are known, there remains a need for more effective topical and microchanneling treatment formulations for the prevention and treatment of many skin conditions, and in particular the prevention and treatment of hyperpigmentation.

SUMMARY OF THE DISCLOSURE

A composition for treating skin hyperpigmentation is disclosed that includes 2 wt %-8 wt % cysteamine, 2 wt %-8 wt % tranexamic acid, 1 wt %-7 wt % niacinamide, 0.1 wt %-2 wt % tetrapeptide 30, 0.1 wt %-2 wt % phytosomes, 0.3 wt % to 1 wt % roxisomes, 0.1 wt %-2 wt % ultrasomes, and a plurality of recombinant human growth factors selected from the group of sh-polypeptide-1, sh-polypeptide-11, sh-polypeptide-31, sh-oligopeptide-2, sh-polypeptide-10, sh-polypeptide-5, sh-polypeptide-8, sh-polypeptide-3, sh-polypeptide-62, acetyl octapeptide-17 amide, sh-oligopeptide-1, sh-polypeptide-4, and acetyl sh-oligopeptide77 amide, wherein the plurality of recombinant human growth factors have in combination a concentration ranging from 0.001 wt % to 1 wt %.

The tetrapeptide 30 may include L-prolyl amino acid, L-lysyl amino acid, L-alpha-glutamyl amino acid, and L-lysine amid acid linked together.

The composition may also include water, glyceryl stearate citrate, tocopherol, and trisodium dicarboxymethyl alaninateone.

In another aspect, a composition for treating skin hyperpigmentation includes about 5 wt % tranexamic acid, about 4 wt % niacinamide, about 0.20 wt % phytic acid, about 2.5 wt % cysteamine hydrochloride, about 1 wt % plankton extract, about 1 wt % lecithin, about 1 wt % *Arabidopsis thaliana* extract, about 1 wt % *micrococcus* lysate, about 0.01 wt % of recombinant human growth factors one or more from the group consisting of sh-polypeptide-62, sh-polypeptide-1, sh-polypeptide-11, sh-polypeptide-31, acetyl octapeptide-17 amide, sh-oligopeptide-2, sh-polypeptide-10, and acetyl sh-oligopeptide-77, and about 1 wt % tetrapeptide-30.

Additionally, a composition for treating skin hyperpigmentation includes about 5 wt % tranexamic acid, about 4 wt % niacinamide, about 0.20 wt % phytic acid, about 5 wt % cysteamine hydrochloride, about 1 wt % plankton extract, about 1 wt % lecithin, about 1 wt % *Arabidopsis thaliana* extract, about 1 wt % *micrococcus* lysate, about 0.01 wt % of recombinant human growth factors one or more from the group consisting of sh-polypeptide-62, sh-polypeptide-1, sh-polypeptide-11, sh-polypeptide-31, acetyl octapeptide-17 amide, sh-oligopeptide-2, sh-polypeptide-10, and acetyl sh-oligopeptide-77, and about 1 wt % tetrapeptide-30.

A method of reducing the appearance of hyperpigmentation is disclosed that includes identifying a target portion of skin exhibiting hyperpigmentation and applying an effective amount of a skin care composition to the target portion of skin over a course of a treatment period. The skin care composition comprises about 5 wt % tranexamic acid, about 4 wt % niacinamide, about 0.20 wt % phytic acid, about 5 wt % cysteamine hydrochloride, about 1 wt % plankton extract, about 1 wt % lecithin, about 1 wt % *Arabidopsis thaliana* extract, about 1 wt % *micrococcus* lysate, about 0.01 wt % of recombinant human growth factors one or more from the group consisting of sh-polypeptide-62, sh-polypeptide-1, sh-polypeptide-11, sh-polypeptide-31, acetyl octapeptide-17 amide, sh-oligopeptide-2, sh-polypeptide-10, and acetyl sh-oligopeptide-77, and about 1 wt % tetrapeptide-30.

DETAILED DESCRIPTION

Compositions for skin creams and serums are provided for treating skin hyperpigmentation, the compositions including cysteamine, tranexamic acid, niacinamide, tetrapeptide 30, DNA repair enzymes, and human growth factors.

In an embodiment, a formulation for a skin cream or serum includes 5% cysteamine by weight, 5% tranexamic acid by weight, 4% niacinamide by weight, 1% tetrapeptide 30 by weight, in which the tetrapeptide 30 includes the following four amino acids linked together: L-prolyl-L-lysyl-L-alpha-glutamyl-L-lysine. In addition, the cream or serum includes DNA repair enzymes, including 1% phytosomes, 0.3 to 1% roxisomes, and 1% ultrasomes. Further, the composition may include recombinant human growth factors, including a plurality of recombinant human growth factors selected from sh-polypeptide-1, sh-polypeptide-11, sh-polypeptide-31, sh-oligopeptide-2, sh-polypeptide-10, sh-polypeptide-5, sh-polypeptide-8, sh-polypeptide-3, sh-polypeptide-62, acetyl octapeptide-17 amide, sh-oligopeptide-1, sh-polypeptide-4, and acetyl sh-oligopeptide77 amide, in which these growth factors are present at a concentration ranging from 0.001% to 1% by weight of the cream or serum. Highly branched cyclic dextrin may also be included, as well as water as a base solvent and other inactive ingredients.

In additional embodiments, the skin cream and serum compositions include 2%-8% cysteamine by weight, 2%-8% tranexamic acid by weight, 1%-7% niacinamide by weight, 0.1%-2% tetrapeptide 30 by weight, in which the tetrapeptide 30 includes the following four amino acids linked together: L-prolyl-L-lysyl-L-alpha-glutamyl-L-lysine. In addition, the composition includes DNA repair enzymes, including 0.1%-2% phytosomes, 0.1%-2% roxisomes, and 0.1%-2% ultrasomes. Further, the composition may include recombinant human growth factors, including one or more recombinant human growth factors selected from sh-polypeptide-1, sh-polypeptide-11, sh-polypeptide-31, sh-oligopeptide-2, sh-polypeptide-10, sh-polypeptide-5, sh-polypeptide-8, sh-polypeptide-3, sh-polypeptide-62, acetyl octapeptide-17 amide, sh-oligopeptide-1, sh-polypeptide-4, and acetyl sh-oligopeptide77 amide, in which such growth factors are present at a concentration ranging from 0.001% to 2% by weight, and highly branched cyclic dextrins.

In another embodiment, the skin cream and serum compositions include 2%-8% cysteamine by weight, 2%-8% tranexamic acid by weight, 1%-7% niacinamide by weight, 0.1%-2% tetrapeptide 30 by weight, in which the tetrapeptide 30 includes the following four amino acids linked together: L-prolyl-L-lysyl-L-alpha-glutamyl-L-lysine. In addition, the composition includes DNA repair enzymes, including 0.1%-2% phytosomes, 0.1%-2% roxisomes, and 0.1%-2% ultrasomes. Further, the composition may include exosomes containing human growth factors, and highly branched cyclic dextrins.

The serums and creams may include additional ingredients such as a base solvent, preferably water and more preferably deionized water, emulsifiers, emollients, skin moisturizing compounds, emulsion thickeners, odor masking agents, chelating agents, and preservatives. The base solvent may comprise more than 50 wt % of the composition.

In another embodiment, the skin cream or serum contains 5 wt % tranexamic acid, 4 wt % niacinamide, 0.20 wt % phytic acid, 5 wt % cysteamine hydrochloride, 1 wt % plankton extract, 1 wt % lecithin, 1 wt % *Arabidopsis thaliana* extract, 1 wt % *micrococcus* lysate, 0.01 wt % a combination of one or more of sh-polypeptide-62, sh-polypeptide-1, sh-polypeptide-11, sh-polypeptide-31, acetyl octapeptide-17 amide, sh-oligopeptide-2, sh-polypeptide-10, and acetyl sh-oligopeptide-77, and 1 wt % tetrapeptide-30. Other ingredients may include a base solvent (e.g., 58 wt %), emulsifiers (e.g., 7 wt %), emollients (e.g., 2 wt %), skin moisturizing compounds (e.g., 6.2 wt %), emulsion thickeners (5 wt %), odor masking agents (e.g., 2 wt %), chelating agents (e.g., 0.1 wt %), and preservatives (e.g., 1 wt %). In a preferred embodiment, the base solvent is water; emulsifiers include glyceryl stearate citrate, cetearyl alcohol; glyceryl caprylate, hydrogenated lecithin, C12-16 alcohols, or palmitic acid; emollients include seed oil, skin moisturizing compounds include tocopherol, vegetable oil, glycerin, or oat beta glucan; and chelating agents include trisodium dicarboxymethyl alaninate.

In another embodiment, the skin cream and serum contains 5 wt % tranexamic acid, 4 wt % niacinamide, 0.20 wt % phytic acid, 2.5 wt % cysteamine hydrochloride, 1 wt % plankton extract, 1 wt % lecithin, 1 wt % *Arabidopsis thaliana* extract, 1 wt % *micrococcus* lysate, 0.01 wt % a combination of one or more of sh-polypeptide-62, sh-polypeptide-1, sh-polypeptide-11, sh-polypeptide-31, acetyl octapeptide-17 amide, sh-oligopeptide-2, sh-polypeptide-10, and acetyl sh-oligopeptide-77, and 1 wt % tetrapeptide-30. Other ingredients may include a base solvent (e.g., 60 wt %), emulsifiers (e.g., 7 wt %), emollients (e.g., 2 wt %), skin moisturizing compounds (e.g., 6.2 wt %), emulsion thickeners (5 wt %), odor masking agents (e.g., 2 wt %), chelating agents (e.g., 0.1 wt %), and preservatives (e.g., 1 wt %). In a preferred embodiment, the base solvent is water; emulsifiers include glyceryl stearate citrate, cetearyl alcohol; glyceryl caprylate, hydrogenated lecithin, C12-16 alcohols, or palmitic acid; emollients include seed oil, skin moisturizing compounds include tocopherol, vegetable oil, glycerin, or oat beta glucan; and chelating agents include trisodium dicarboxymethyl alaninate.

Serums and creams having the compositions described above may be applied to areas to be treated via either a microchanneling process, or topically, or both, as indicated, such as once or twice per day, for improving skin hyperpigmentation.

The term "about" when used with a corresponding numeric value refers to +20% of the numeric value, typically ±10% of the numeric value, often ±5% of the numeric value, and most often ±2% of the numeric value. In some embodiments, the term "about" can be taken as exactly indicating the actual numerical value.

Various modifications and additions can be made without departing from the spirit and scope of this disclosure. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present disclosure. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this invention.

What is claimed is:

1. A composition for treating skin hyperpigmentation consisting of:
    about 5 wt % tranexamic acid;
    about 4 wt % niacinamide;
    about 0.20 wt % phytic acid;
    about 5 wt % cysteamine hydrochloride;
    about 1 wt % plankton extract;
    about 1 wt % lecithin;
    about 1 wt % *Arabidopsis thaliana* extract;
    about 1 wt % micrococcus lysate;
    about 0.01 wt % of one or more recombinant human growth factors selected from the group consisting of sh-polypeptide-62, sh-polypeptide-1, sh-polypeptide-11, sh-polypeptide-31, acetyl octapeptide-17 amide, sh-oligopeptide-2, sh-polypeptide-10, and acetyl sh-oligopeptide-77;
    about 1 wt % tetrapeptide-30;
    about 60 wt % base solvent;
    about 7 wt % emulsifiers;
    about 2 wt % emollients;
    about 6.2 wt % skin moisturizing compounds;
    about 5 wt % emulsion thickeners;
    about 2 wt % odor masking agents;
    about 0.1 wt % chelating agents; and
    about 1 wt % preservatives.

2. The composition of claim 1, wherein the base solvent is water.

* * * * *